United States Patent [19]

Hellstrom

[11] 4,139,776

[45] Feb. 13, 1979

[54] SYSTEM FOR CIRCULAR AND COMPLEX TOMOGRAPHY

[75] Inventor: Melbourne J. Hellstrom, Severna Park, Md.

[73] Assignee: CGR Medical Corporation, Baltimore, Md.

[21] Appl. No.: 835,738

[22] Filed: Sep. 22, 1977

[51] Int. Cl.² .................................. G03B 41/16
[52] U.S. Cl. .......................... 250/445 T; 250/402; 250/491
[58] Field of Search ............... 250/445 T, 490, 491, 250/401, 402

[56] References Cited

U.S. PATENT DOCUMENTS

| | | | |
|---|---|---|---|
| 3,809,886 | 5/1974 | Cochran | 250/445 T |
| 4,087,694 | 5/1978 | Hellstrom | 250/445 T |

Primary Examiner—Craig E. Church
Attorney, Agent, or Firm—Brady, O'Boyle & Gates

[57] ABSTRACT

A system for conducting circular as well as complex tomographic procedures utilizing apparatus which has no mechanical linkage between the X-ray source and the X-ray receptor. The path of travel of the X-ray source both circularly and linearly is sensed by electromagnetic radiation and more particularly by light radiation which is generated by a laser. The linear travel is sensed by means of reflected laser radiation directed to the X-ray source and fed to an interferometer. The circular travel, on the other hand, is sensed by means of a laser gyroscope also receiving light radiation from a laser. Optical energy sensing means is thus used to generate command signals which are coupled to respective drive motors which act to rotate and when desirable, translate the X-ray receptor so that its motion follows the motion, both orbital and linear, of the X-ray source for performing any desired type of tomographic procedure.

23 Claims, 3 Drawing Figures

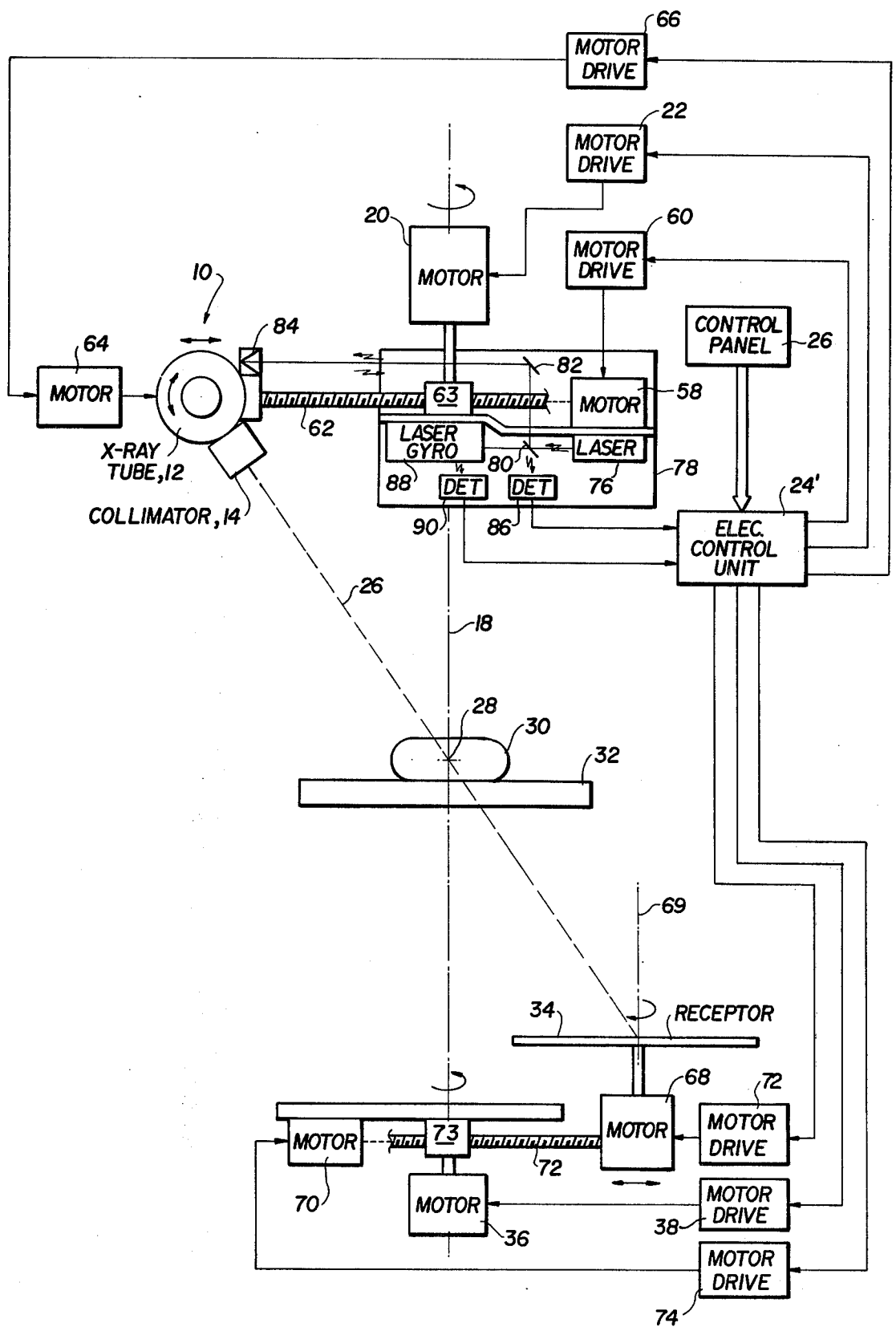

SYSTEM FOR CIRCULAR AND COMPLEX TOMOGRAPHY

CROSS REFERENCES TO RELATED APPLICATION

This invention is related to the linear tomography system disclosed in U.S. Pat. No. 4,087,694, entitled "Tomography System", being filed on Sept. 20, 1976 and issuing on May 2, 1978 in the name of M. J. Hellstrom, et al., which application patent is also assigned to the assignee of the present invention.

Reference is also made to a related application assigned to the present assignee, which is U.S. Ser. No. 739,017, entitled "Motorized Bucky" filed in the name of Laverne R. Bunch, on Nov. 4, 1976.

BACKGROUND OF THE INVENTION

This invention relates generally to apparatus for performing tomography and more particularly to an electronically controlled tomography system which has no mechanical linkage between the source and image receptor and which in addition utilizes electromagnetic (laser) radiation for sensing both circular and linear motion of the X-ray source during a tomographic procedure.

Present systems for performing complex tomographic procedures including circular and trispiral motions, for example, require massive and complex precision mechanical linkages between the X-ray beam source and the X-ray receptor which may comprise a film holder or bucky so that their relative motions can be precisely controlled with regard to the patient or object under test.

In the above-cross-referenced U.S. Pat. 4,087,694, there is described in a linear tomographic system including means for eliminating the conventional mechanical linkage between an overhead tube suspension and a bucky in an X-ray table. It includes a source of laser light radiation directed to the X-ray source for sensing the position and translation of the source and generating control signals in accordance with the sensed translation to move the bucky proportionately in the opposite direction as well as additionally tilting the X-ray source so that the central ray therefrom turns about the focal spot of the source and accordingly points approximately to the same location on the film. In a specific embodiment of the system disclosed, a helium-neon laser directs a beam of monochromatic optical light through a beam splitter to a rectroreflector located on the X-ray tube for sensing the position of the X-ray tube's focal spot at a location which is fixed relative to the focal spot whereupon the reflected light is directed back to the interferometer which produces an interference fringe pattern output which corresponds to the linear translation of the X-ray tube. An electrical pulse train is generated from the output of a photodetector exposed to the fringe pattern, which is then utilized to generate a motor drive signal for an electrical motor coupled to the bucky which then is driven linearly in an opposite direction with respect to the X-ray tube.

One other means is known for performing a tomographic procedure which obviates the need for mechanical linkage between the X-ray source and the receptor. Such apparatus is disclosed in U.S. Pat. No. 3,809,886, entitled "Dynamic Tomography With Movable Table", Cochran, et al. which issued on May 7, 1974. In this patent the support member as opposed to the film holder is moved in synchronism with the source and the source is energized at time intervals which define the several successive positions filmed.

SUMMARY

Briefly, the subject invention is an improvement over the cross referenced U.S. Pat. No. 4,087,694, in that complex procedures can now be performed while still not requiring mechanical coupling between the X-ray source and image receptor.

The improvement comprises utilizing laser gyroscope means for sensing the orbital movement of the radiological, i.e. X-ray beam source about an axis of rotation which passes through a predetermined fulcrum point intermediate the source and receptor. The laser gyroscope generates an interferometric fringe pattern in response to angular displacement. The fringe pattern is detected providing an electrical pulse train which is utilized to operate a circular drive motor coupled to the image receptor which is also adapted to rotate about the same axis of rotation. Accordingly, synchronized equal angular displacements of the beam source and receptor are accomplished as the source orbits about the axis. The central ray of the X-ray beam generated by the source also passes through the fulcrum point at a predetermined tilt angle relative to the axis of rotation and is projected so that it points to approximately the center of the image receptor. The receptor itself is caused to rotate about its own axis which is offset relative to the axis of rotation in the opposite direction as it orbits about the axis of rotation in order to maintain a constant orientation relative to the X-ray source and the subject under examination. This rotational motion combined with the linear motion apparatus described in U.S. Pat. No. 4,087,694, permits any predetermined or selected tomographic scan pattern to be accomplished.

BRIEF DESCRIPTION OF THE DRAWINGS

FIG. 3 is an electromechanical block diagram illustrative of an embodiment of the subject invention for performing complex tomography.

DESCRIPTION OF THE PREFERRED EMBODIMENT

Figure 1:
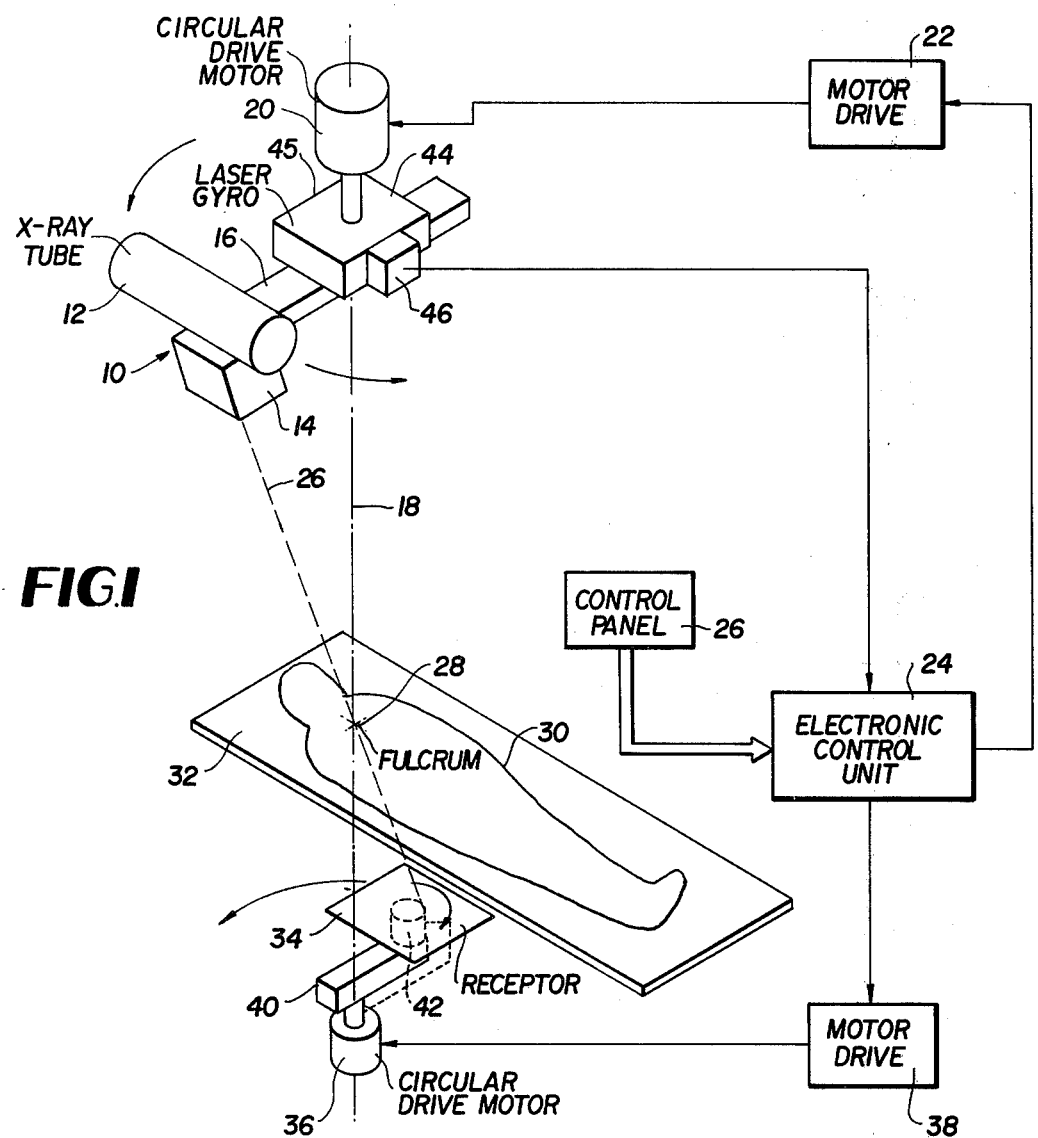
FIG. 1 is an electromechanical block diagram illustrative of the embodiment of the subject invention for performing circular tomography.

Referring now to the drawings, and more particularly to FIG. 1, reference numeral 10 designates an X-ray beam source assembly including an X-ray tube 12 and a collimator 14. This assembly is mounted on a radial arm support member 16 which is adapted to be driven in an arcuate but more particularly a circular path about an axis of rotation 18 which is generally but not restricted to being vertical. This planar rotation is provided by a circular drive motor 20 mounted, for example, on a ceiling assembly, not shown, or as a second example to a floor mounted support. Such ceiling assemblies are conventional and is shown in a broad sense in the aforementioned related application, U.S. Pat. No. 4,087,694. The circular drive motor 20 is coupled to and is driven by a motor drive circuit 22, which in turn is coupled back to an electronic control unit 24, which is adapted to operate in accordance with operator selected procedure provided on a control panel 26.

The X-ray source assembly 10 is radially offset from the rotational axis 18 and is tilted at a predetermined control angle relative thereto so that the central ray 26 of the X-ray radiation from the tube source 12 intersects the axis 18 at a fulcrum point 28 and the center of an image receptor 34. The fulcrum point 28 consists of the region under investigation within a patient 30, for example, positioned on a radiological examination table 32.

Beneath the table 32 is located an X-ray beam receptor 34, which may be, for example, a film holder, image intensifier or other device(s) responsive to X-ray energy for providing a suitable X-ray image of the region under investigation. The receptor means 34 is also adapted to orbit the axis 18 in a circular path in a plane parallel to the plane of travel of the source assembly 10. This movement is provided by a second circular drive motor 36 and its respective motor drive circuit 38, which also receives its control from the electronic control unit 24. The axis of rotation of the circular drive motor 36 is aligned with the circular drive motor 24 along the axis 18. The receptor means 34 is radially offset from the axis 18 by means of a radial support member 40 coupled to the shaft of the drive motor 36. Intermediate the support member 40 and the receptor means 34 is a means 42 which may be, for example, a mechanism or electric motor which is coupled back to the circular motor drive 36 or its shaft for keeping the orientation of the receptor means 34 constant relative to the table top or more importantly the subject of the examination, the patient.

It is the purpose of the subject invention to slave i.e. synchronize the motion both angular and linear of the receptor means 34 to the predetermined motion of the source assembly 10 in response to an operator selected sequence. While the cross referenced related application U.S. Pat. No. 4,087,694 discloses means for slaving the linear displacement of the image receptor to the source, the embodiment in FIG. 1 is adapted to slave angular motion of an image receptor to the source. This is accomplished by sensing the angular rotation of the source 10 about the axis 18 and then positioning the support arm 40 and driving the circular drive motor 36 coupled to the receptor means 34 so that their relative positions are locked.

The means for sensing the angular rotation of the X-ray source assembly 10 about the axis 18 is provided by laser gyroscope means 44 which is operable to generate an interference fringe pattern as a function of angular rotation. Such means, per se, are well known in the art, typical examples being shown and disclosed in U.S. Pat. Nos. 3,373,650, Kilpatrick; 3,467,472, Kilpatrick; 3,392,622, Senf; and 3,535,040, Vigneri. In such apparatus often referred to as laser angular sensors, two monochromatic beams of monochromatic light are directed in opposite directions about a closed loop path which encloses the axis of rotation about which the angular motion is to be sensed. Rotation of the apparatus about this axis causes an effective path length change for each beam and thus produces a frequency difference between the two beams and accordingly a fringe pattern is produced since the frequency of oscillation of the laser is dependent upon the length of the laser path. The magnitude and the sign of this difference in frequency are indicative not only of the rate, but of the direction of rotation and consequently can be detected to provide a measure of angular position or angular rate, depending upon the needs of the user.

The laser gyroscope 44 accordingly includes within its housing 45 a laser source as well as two light conducting rods or fibers, not shown, wound in opposite directions and being directed to a photodetector 46 which is adapted to generate an electrical output pulse signal corresponding to the phase reversal of the fringe pattern generated, and thus provide an indication of angular movement of the X-ray source assembly 10 as it moves, i.e. orbits about the vertical axis 18.

Accordingly any rotational movement of the X-ray tube assembly 10 causes the photodetector 46 to produce a pulse output signal which corresponds to the reversal of the fringe pattern produced by the laser gyroscope. This pulse signal is fed to the amplifier circuit 48. The amplified pulses are fed to a pulse divider which divides the pulse train by a predetermined factor N for providing an output having a readily usable pulse repetition rate. The output of the pulse divider 50 is coupled to a programmable counter circuit 52 controlled by a microprocessor 54 which has operator selected inputs coupled thereto from the control panel 26 in a manner disclosed in U.S. Pat. No. 4,087,694. A memory 56 is intercoupled with the microprocessor 54 such that the selected input parameters cause the programmable counter 52 to feed a control signal to the motor drive circuit 38 which may be, for example, a circuit adapted to operate a step motor. With the circular drive motor 36 then being a step motor, it incrementally drives the image receptor 34 so that it follows the position of the source assembly 10 while being 180° out of phase therewith so as to be on the opposite side of the rotational axis 18. Accordingly, a circular tomographic procedure is effected without mechanical linkage or the table being moved, the latter being taught in the prior art Cochran, et al. patent, U.S. Pat. No. 3,809,886.

Referring now to FIG. 3, there is disclosed an electromechanical block diagram illustrative of a tomographic system which is adapted to provide both circular motion and linear motion in the radial direction, and thereby carry out complex tomographic procedures according to any desired scan pattern. As in the embodiment shown in FIG. 2, the desired tomographic sequence of motion is operator selected on the control panel 26 which sends instructions to the electronic control unit 24' which causes its microprocessor, not shown, to cause not only the circular drive motor 20 to operate through signals coupled thereto by means of the motor drive circuit 22, but also to a linear drive motor 58 which may be, for example, an electrical step motor driven by its respective motor drive circuit 60. The step motor 58 is mechanically coupled to and is adapted to drive a ball screw member 62 which feeds through a bearing block 63 to the X-ray source 10 including the X-ray tube 12 and the collimator 14. A third motor 64 is also driven by the electronic control unit 24' through its respective drive motor circuit 66 for providing the required tilt angle of the X-ray tube 12 for directing the central beam 26 through the fulcrum point 28 depending upon the radial linear distance away from the circular rotational axis 18. When desirable, a mechanical linkage may be used to rotate the X-ray tube as it is translated by the linear drive.

It should also be pointed out that if the X-ray source 10 shown in FIG. 1 is adapted to have a radially adjustable support arm member 16, a motor 64 such as shown in FIG. 3 would also be utilized for automatically adjusting the proper tilt angle of the X-ray tube 12. Thus depending upon the use to which it is put, the angle of tilt of the X-ray tube 12 can be either fixed or adjustable.

Referring now back to the embodiment shown in FIG. 3, the receptor 34 is adapted to be electrically linked to the motion of the X-ray source 10 by means of two circular drive motors and one linear translation motor. More particularly, a first rotational drive motor 36 which is identical to that shown in FIG. 1 is adapted to rotate the receptor about the axis 18. A second rotational drive motor 68 is adapted to rotate the receptor 34 in an opposite direction about its own axis 69 as the receptor orbits the axis 18. The motor 68, however, can be replaced when desirable by a mechanical coupling since its rotation is always equal and opposite to that of the motor 36. The third motor 70 is a linear drive motor which is mechanically coupled to a ball screw shaft 72 which is mechanically coupled to the motor 68 through a bearing block 73 for varying the radius arm or offset position of the receptor 34 so that the central beam 26 is adapted to strike the center thereof in response to any radial change of the source assembly 10. The three motors are preferably comprised of step motors being driven through respective motor drive circuits 38, 72 and 74 by means of suitable control signals coupled thereto from the electronic control circuit 24'.

The radial linear displacement of the X-ray source 10 is sensed in a manner similar to that disclosed in the aforementioned U.S. Pat. No. 4,087,694 except in the instant embodiment the laser source 76 which may be, for example, a helium neon laser, is mounted on the mechanical assembly 78 which may for example be the tube stand as opposed to being located off or remote from the apparatus. The assembly 78 is also adapted to contain the apparatus such as the linear drive motor 58 and the ball screw assembly 62.

An interferometer consisting of a partially reflective mirror 80 mounted on the assembly 78 is adapted to transmit laser light from the laser 76 to a mirror device 82 which is adapted to be positioned in line with an optical reflector 84 which is mounted on the X-ray tube 12 in such a manner that it will keep a constant orientation facing the mirror 82 irrespective of the tilt of the X-ray tube 12. Accordingly, the linear or radial displacement of the X-ray tube 12 from the axis 18 and accordingly the mirror 82 will generate an interference fringe pattern at the partially reflective mirror 80. The fringe pattern is coupled to a photodetector 86 which is adapted to provide an electrical pulse train output in response to the fringe pattern. The electronic control unit 24' will then cause the motor drive circuit 74 to cause the linear drive motor 70 to linearly displace the receptor 34 by rotation of ball screw shaft 72.

As in the embodiment shown in FIG. 1, the rotational or angular displacement of the X-ray source 10 relative to the rotational axis 18 is sensed by means of a laser gyroscope assembly 88 which is adapted to receive its required optical energy input from the laser source 76 through the partially reflective mirror 80. As in the embodiment described with reference to FIG. 1, the laser gyro assembly 88 will generate an interference fringe pattern in response to the angular displacement of the X-ray source 10 with respect to the axis 18. The fringe pattern from the laser gyro assembly 88 is coupled to a second photodetector 90 which is also adapted to produce an electrical pulse train in response to the fringe pattern sensed, which pulse train is fed to the electrical control unit 24' which is adapted to operate in a manner shown in FIG. 2 to couple drive signals to the motor drive circuits 38 and 72, respectively, to effect angular displacement of the receptor 34 in synchronism with the angular movement of the source 10 as well as rotating the receptor 34 in the opposite direction so as to maintain a constant orientation of the receptor as it moves in a circular plane beneath the X-ray table 32.

Figure 2:
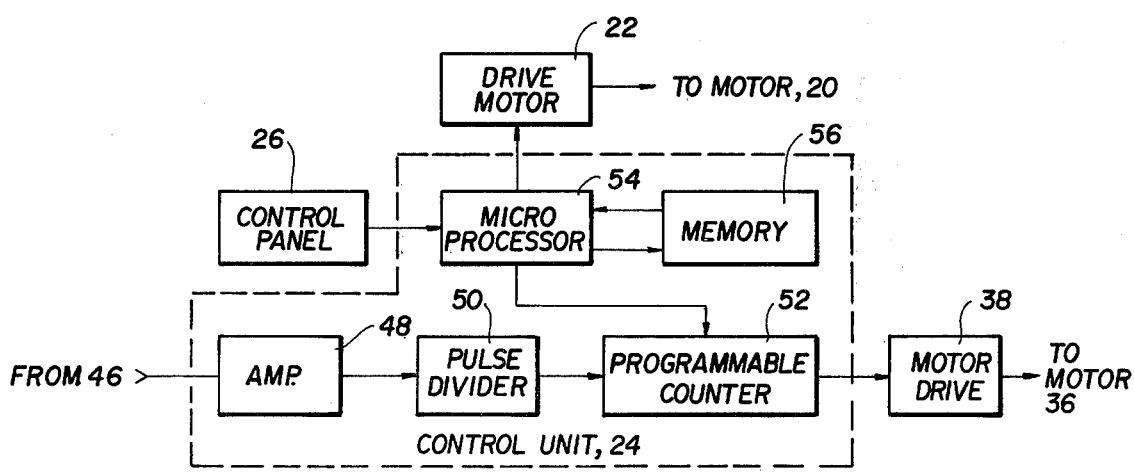
FIG. 2 is an electrical block diagram illustrative of an electronic control circuitry incorporated in the subject invention.

While not described in detail in the foregoing description, the fulcrum level is determined by the interrelationship of the servo type motion of the receptor 34 in response to the motion of the X-ray source 10. Accordingly, the fulcrum level selected by the operator causes the memory 56 (FIG. 2) to couple programming inputs to the microprocessor 54 dependent upon the sweep parameter selected to cause a respective output count of one or more programmable counters such as the programmable counter 52 as shown in FIG. 2 to change the proper relationship of proportional speed between the motors generating the desired tomographic motion between the X-ray tube 12 and the receptor 34.

Thus what has been shown and described are the essential elements of a complex tomographic system with non-mechanical coupling between the X-ray source and the receptor with the respective motions being mutually tied together as a result of the angular and radial components of motion sensed by optical laser assemblies which are particularly adapted to measure relatively small incremental changes in the position of the devices which they are intended to monitor. It should be pointed out that the system of the present invention is adapted for completely general motions involving almost any arbitrary relationships between the angular displacements and radial displacements of the source and image receptor.

While there has been shown and described what is at present considered to be the preferred embodiments of the subject invention, further modifications thereto will readily occur to those skilled in the art. It is not desired, therefore, that the invention be limited to the specific steps and arrangements shown and described, but it is to be understood that all equivalents, alterations and modifications coming within the spirit and scope of the present invention as set forth in the following claims are herein meant to be included.

I claim:

1. A method for non-mechanically linking the motion of an X-ray source unit with an X-ray receptor unit during a tomographic procedure comprising the steps of:

effecting motion of one of said units in an angular displacement path about an axis passing through a predetermined fulcrum point intermediate the source unit and the receptor unit;

sensing the means of radiant energy a parameter which is a function of the angular displacement of said one unit about said axis and generating a parameter signal therefrom;

generating a command signal in response to said parameter signal and applying said command signal to said other unit for effecting an in-line position through said fulcrum point relative to said one unit on the opposite side of said axis and causing said other unit to effect angular displacement in synchronism with said one unit in mutually parallel planes on the opposite side of said fulcrum point.

2. The method as defined by claim 1 wherein said step of sensing includes sensing the circular displacement of said one unit about said axis.

3. A method as defined by claim 1 wherein said step of effecting angular displacement comprises angularly moving said X-ray source unit in an angular path about said axis.

4. The method as defined by claim 1 wherein said radiant energy comprises optical energy.

5. The method as defined by claim 4 wherein said sensing step consists in directing two beams of optical energy in opposite directional paths around said axis thereby generating an interference fringe pattern at a common output in response to the angular displacement;
   detecting said fringe pattern; and
   generating said parameter signal in response to detecting said interference fringe pattern.

6. The method as defined by claim 4 wherein said sensing step comprises directing a source of coherent light in opposite directions in respective paths around said axis and interferometrically combining the light energy at a selected point in an interference fringe pattern; and
   generating said command signal in response to said interference fringe pattern.

7. The method as defined by claim 6 wherein said source of coherent light comprises a laser.

8. The method as defined by claim 1 and additionally including the steps of:
   effecting translational motion of said one unit simultaneously with the angular displacement thereof;
   sensing by means of radiant energy a parameter which is a function of the translational motion of said one unit and generating another parameter signal therefrom;
   generating another command signal in response to said another parameter signal; and
   applying said another command signal to said other unit for effecting a colinear position and translational motion in an opposite direction with respect to said one unit.

9. The method as defined by claim 8 wherein said steps of sensing both angular and translational motion of said one unit comprises sensing by the angular displacement and translational movement of said X-ray source unit.

10. The method as defined by claim 9 wherein said sensing steps comprise sensing by optical energy radiation the angular and translational motion of said X-ray source unit.

11. The apparatus for making tomographs including an X-ray source means and an X-ray receptor means, both of which are adapted to orbitally move in synchronism about an axis passing through an intermediate predetermined fulcrum point during a tomographic procedure, the improvement comprising, in combination:
   first and second drive means respectively coupled to and being operable to simultaneously move said source means and said receptor means in parallel arcuate paths which are mutually offset from said axis and on opposite sides thereof in response to respective command signals applied thereto;
   first circuit means coupling an arcuate path command signal to one of said first and second drive means in response to at least one input parameter selected for a predetermined tomographic procedural sequence;
   radiant energy angular displacement sensing means selectively positioned on said apparatus and being operable to sense the angular displacement of the means driven by said one drive means and providing an output signal in accordance with the angular displacement of said driven means about said axis; and
   second circuit means coupled to said output signal and being responsive thereto to provide a command signal coupled to the other of said first and second drive means to effect an arcuate path follower movement of the means driven thereby.

12. The apparatus as defined by claim 11 wherein said angular displacement sensing means senses the angular displacement of said X-ray source means and said means driven by said other drive means comprises the receptor means.

13. The apparatus as defined by claim 12 wherein said angular displacement sensing means comprises optical energy sensing means.

14. The apparatus as defined by claim 12 wherein said optical energy sensing means comprises laser gyroscope means.

15. The apparatus as defined by claim 12 and additionally including means responsive to said other drive means to provide rotation of said receptor means about an axis parallel to said axis passing through said fulcrum point and having a direction of rotation opposite to the direction of angular displacement of said receptor means in order to maintain a substantially constant orientation of said receptor means relative to the subject being examined as the source means and receptor means orbits about said axis passing through said fulcrum point.

16. The apparatus as defined by claim 11 wherein said angular displacement sensing means comprises a coherent light source and bidirectional light conducting path means coupled to said light source and being adapted to provide an interference fringe pattern output in response to said angular displacement of said driven means, and means responsive to said interference fringe pattern to provide a pulse signal output in accordance with the phase reversals of the optical energy contained in said interference fringe pattern.

17. The apparatus as defined by claim 11 wherein said first and second drive means comprises a respective electrical motor and motor drive circuit therefor for providing orbital motion of said source means and said receptor means about said axis on opposite sides of said fulcrum point.

18. The apparatus as defined by claim 17 wherein said first circuit means comprises control circuit means coupled to said source means motor drive circuit, said control circuit means including a microprocessor and a memory intercoupled thereto and being operable in response to operate selected operational mode to command a predetermined orbital rotation of said driven means operated by said one drive means.

19. An apparatus for making tomographs including an X-ray source means and receptor means, both of which are adapted to move in arcuate paths synchronously in offset relationship in mutually parallel planes about an axis passing through an intermediate fulcrum point, as well as move in parallel linear paths in mutually opposite directions such that the line from the focal spot of the X-ray source means to the center of the image receptor passes through said fulcrum point during a tomographic procedure, the improvement comprising, in combination:

first and second drive means respectively coupled to and being operable to simultaneously rotate said source means and said receptor means in respective parallel paths while being on the opposite side of said axis in response to rotational command signals applied thereto;

third drive means coupled to and being operable to tilt said source means in response to a tilt command signal applied thereto;

first circuit means coupling an arcuate path orbital command signal to one of said first and second drive means in response to at least one input parameter selected for a predetermined tomographic procedural sequence;

first radiant energy sensing means selectively positioned on said apparatus and operable to sense the angular displacement effected by the driven means coupled to said one drive means, said first sensing means providing first output signal in accordance with the angular displacement of said driven means about said axis;

second circuit means coupled to said first output signal and being responsive thereto to provide an orbital command signal coupled to the other of said first and second drive means to effect a follower orbital path rotation of the means driven thereby;

fourth and fifth drive means respectively coupled to and being operable to simultaneously linearly translate said source means and said receptor means in response to translational command signals applied thereto;

third circuit means coupling a translational command signal to one of said fourth and fifth drive means in response to at least another parameter selected for said tomographical sequence;

second radiant energy sensing means non-mechanically coupled to the means driven by said drive means coupled to said third circuit means and providing a second output signal in accordance with the positional change of said means driven by said one of said fourth and fifth drive means;

fourth circuit means coupled to said second output signal and being responsive thereto to provide a translational command signal coupled to the other of said fourth and fifth drive means to effect a follower translation of the drive means driven thereby; and fifth circuit means coupled to said second output signal and being responsive thereto to provide said tilt command signal coupled to said third drive means.

20. The apparatus as defined by claim 19 and additionally including means coupled to said receptor means for rotating said receptor means about an axis parallel to said axis passing through said fulcrum point in a predetermined direction for maintaining a substantially constant orientation of said receptor means toward the subject under examination during orbital movement of said source means.

21. The apparatus as defined by claim 20 wherein said last recited means comprises sixth drive means coupled to and being operable to rotate said receptor means in response to a rotational command signal applied thereto and sixth circuit means coupled to said first output signal and being responsive thereto to provide a rotational command signal coupled to said sixth drive means to effect a rotation of said receptor means at an angular rate equal to but in opposite direction relative to the orbital movement of said beam source.

22. The apparatus as defined by claim 21 wherein said first and second radiant energy sensing means comprises optical energy means located in the vicinity of said beam source and being respectfully adapted to sense the movement thereof relative to said fulcrum point.

23. The apparatus as defined by claim 21 wherein first radiant energy sensing means comprises a laser gyroscope device.

* * * * *